(12) United States Patent
Shaikh et al.

(10) Patent No.: US 8,990,026 B2
(45) Date of Patent: Mar. 24, 2015

(54) SYSTEM AND METHOD FOR DETECTING COMBUSTION HARDWARE DAMAGE

(75) Inventors: Tauseef Ahmed Shaikh, Maharashtra (IN); Robert Joseph Iasillo, Atlanta, GA (US); Praveen Babulal Jain, Tamil Nadu (IN); KrishnaKumar Pg, Karnataka (IN); Ajith Kizhuthrukovil Radhakrishnan, Kerala (IN); Mallareddy Soudary, Andhra Pradesh (IN)

(73) Assignee: General Electric Company, Schenectady, NY (US)

( * ) Notice: Subject to any disclaimer, the term of this patent is extended or adjusted under 35 U.S.C. 154(b) by 581 days.

(21) Appl. No.: 13/342,764

(22) Filed: Jan. 3, 2012

(65) Prior Publication Data

US 2013/0173181 A1 Jul. 4, 2013

(51) Int. Cl.
*G01B 3/44* (2006.01)
*G01N 29/14* (2006.01)
*G01N 29/04* (2006.01)
*F23N 5/24* (2006.01)
*F23N 5/16* (2006.01)
*F23N 5/00* (2006.01)
*G01M 5/00* (2006.01)

(52) U.S. Cl.
CPC ............ *G01N 29/14* (2013.01); *G01N 29/046* (2013.01); *F23N 5/242* (2013.01); *F23N 5/16* (2013.01); *F23N 5/00* (2013.01); *G01M 5/0033* (2013.01); *G01N 2291/2693* (2013.01)
USPC ............................................. 702/34; 60/722

(58) Field of Classification Search
CPC .......... G01N 2291/2693; G01N 29/14; G01N 29/046; G01M 5/0033; F23N 5/242; F23N 5/16; F23N 5/00
USPC ........................................................ 702/34
See application file for complete search history.

(56) References Cited

U.S. PATENT DOCUMENTS

| | | | |
|---|---|---|---|
| 7,441,411 B2 | 10/2008 | Gleeson et al. | |
| 2004/0176902 A1* | 9/2004 | McBrien et al. | 701/100 |
| 2007/0027607 A1* | 2/2007 | Norris et al. | 701/100 |
| 2007/0062196 A1* | 3/2007 | Gleeson et al. | 60/722 |
| 2008/0134684 A1* | 6/2008 | Umeh et al. | 60/772 |
| 2010/0223933 A1* | 9/2010 | Umeh et al. | 60/794 |
| 2011/0219741 A1* | 9/2011 | Ernst et al. | 60/39.15 |

* cited by examiner

*Primary Examiner* — John Breene
*Assistant Examiner* — Eyob Hagos
(74) *Attorney, Agent, or Firm* — Armstrong Teasdale LLP

(57) ABSTRACT

A power generation plant including a plurality of combustor cans, one or more sensors configured to measure acoustic vibrations from the plurality of combustor cans, and a controller that includes a processor. The processor is programmed to identify a dominant tone of the measured acoustic vibrations, the dominant tone being a frequency where a highest amount of energy lies, determine, for each of the plurality of combustor cans, a frequency of the dominant tone at predefined time intervals, and determine a degradation status of at least one of the plurality of combustor cans based on the frequency of the dominant tone at each of the predefine time intervals for the at least one of the plurality of combustor cans.

20 Claims, 4 Drawing Sheets

SYSTEM AND METHOD FOR DETECTING COMBUSTION HARDWARE DAMAGE

BACKGROUND OF THE INVENTION

The field of the disclosure relates generally to a power generation plant, and more specifically, to a system and method for monitoring gas turbine combustor hardware.

Combustion hardware is critical to an operation of gas turbines. However, issues can develop with combustion hardware in a power plant that results in undesirable operating conditions or even damage to a gas turbine. For example, combustor cans may have mechanical problems relating to fuel nozzles, liners, transient pieces, transient piece sides, radial seals, and/or impingement sleeves. These problems can lead to damage, inefficiencies, or blow outs, which can lead to an unplanned forced outage and collateral damage to a combustion system and the gas turbine. Therefore, to achieve acceptable system durability and reliability, combustion hardware should be carefully monitored and controlled. However, conventional systems for monitoring combustion hardware are not proactive in detecting combustion hardware damage. As such, an alarm triggered by conventional systems is often late and major damage has already been done.

BRIEF DESCRIPTION OF THE INVENTION

In one aspect, a power generation plant is provided. The power generation plant includes a plurality of combustor cans, one or more sensors configured to measure acoustic vibrations from the plurality of combustor cans, and a controller that includes a processor. The processor is programmed to identify a dominant tone of the measured acoustic vibrations, the dominant tone being a frequency where a highest amount of energy lies, determine, for each of the plurality of combustor cans, a frequency of the dominant tone at predefined time intervals, and determine a degradation status of at least one of the plurality of combustor cans based on the frequency of the dominant tone at each of the predefine time intervals for the at least one of the plurality of combustor cans.

In another aspect, a method for monitoring gas turbine combustor hardware is provided. The method includes obtaining acoustic vibration data corresponding to each of a plurality of combustor cans, identifying a dominant tone of acoustic vibrations from the plurality of combustor cans, the dominant tone being a frequency where a highest amount of energy lies, determining, for each of the plurality of combustor cans, a frequency of a dominant tone at predefined time intervals, and determining a degradation status of at least one of the plurality of combustor cans based on the frequency of the dominant tone at each of the predefine time intervals for the at least one of the plurality of combustor cans.

In yet another aspect, a system for monitoring gas turbine combustor hardware is provided. The system includes a combustor comprising a plurality of combustor cans, one or more sensors configured to measure combustion dynamics amplitude data from acoustic vibrations corresponding to each of the plurality of combustor cans, and a controller that includes a processor. The processor programmed to determine frequency data from the measured combustion dynamics amplitude data, identify a dominant tone based on the determined frequency data, the dominant tone being a frequency where a highest amount of energy lies, determine, for each of the plurality of combustor cans, a frequency of the dominant tone at predefined time intervals, and determine a degradation status of at least one of the plurality of combustor cans based on the frequency of the dominant tone at each of the predefine time intervals for the at least one of the plurality of combustor cans.

BRIEF DESCRIPTION OF THE DRAWINGS

The present disclosure is described in detail below with reference to the attached drawing figures.

DETAILED DESCRIPTION OF THE INVENTION

While embodiments of the disclosure are illustrated and described herein with reference to a power generation plant that includes combustion hardware, aspects of the disclosure are operable with any system that performs the functionality illustrated and described herein, or its equivalent.

Combustion hardware is critical to an operation of gas turbines. Thus, to achieve acceptable system durability and reliability, combustion hardware should be carefully monitored and controlled. The present disclosure provides a system and method for identifying combustion hardware damage based on real time gas turbine operating data and combustion dynamics data during a running state of a gas turbine. For example, by monitoring changes in a dominant tone of acoustic vibrations from a plurality of combustor cans, a degradation status of each combustor can may be determined based on a change in a frequency of the dominant tone over a period of time.

An exemplary technical effect of the methods and systems described herein includes at least one of (a) obtaining acoustic vibration data corresponding to each of a plurality of combustor cans; (b) identifying a dominant tone of acoustic vibrations from the plurality of combustor cans, the dominant tone being a frequency where a highest amount of energy lies; (c) determining, for each of the plurality of combustor cans, a frequency of a dominant tone at predefined time intervals; (d) and determining a degradation status of at least one of the plurality of combustor cans based on the frequency of the dominant tone at each of the predefine time intervals for the at least one of the plurality of combustor cans.

Figure 1:
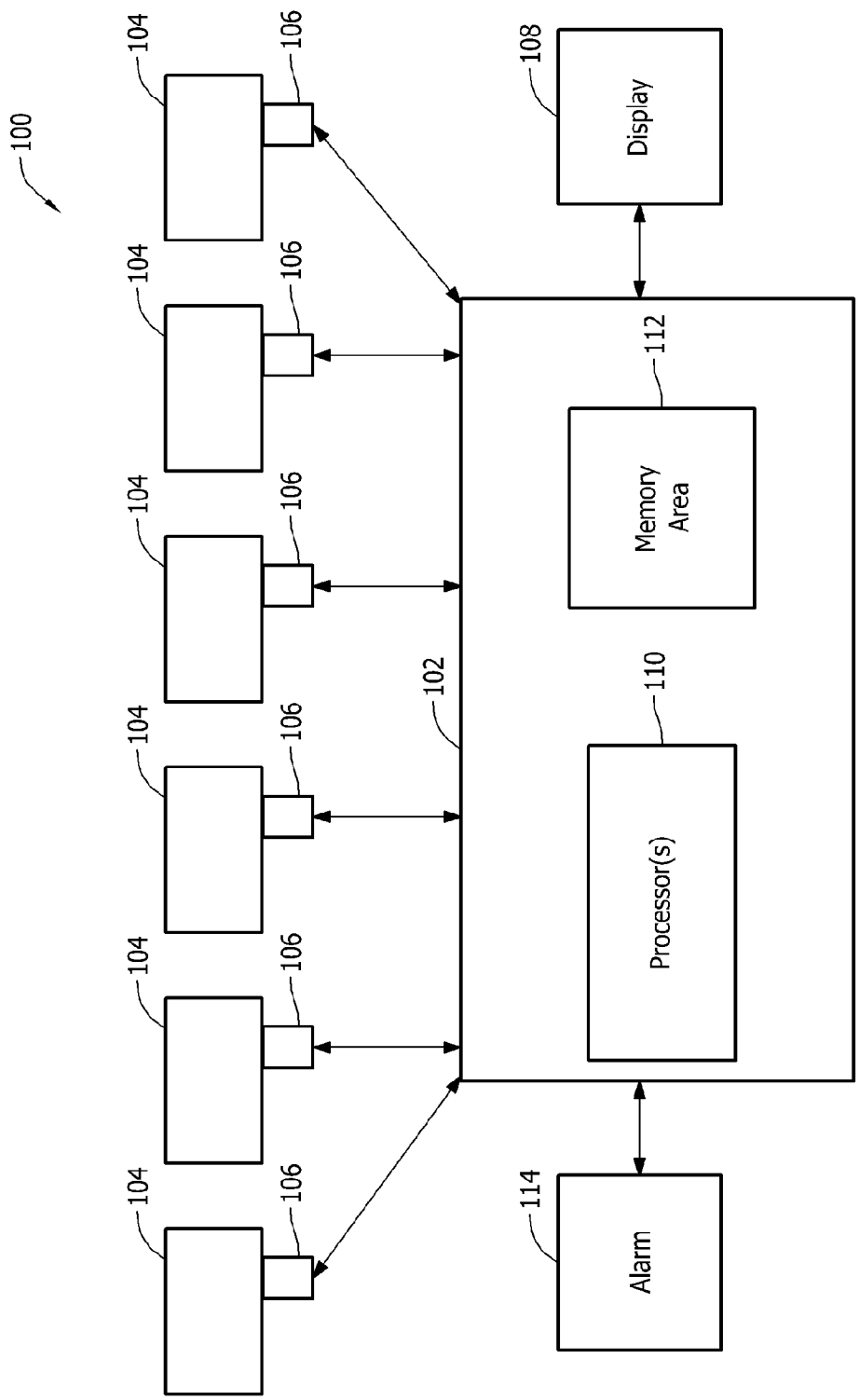
FIG. 1 is a block diagram of a portion of a power generation plant.

With reference to FIG. 1, a block diagram of a power plant (e.g., a gas turbine) 100 that includes a plurality of combustor cans 104 and a plurality of sensors 106 coupled to (e.g., positioned within) a corresponding combustor can 104 is provided. One of ordinary skill in the art guided by the teachings herein will appreciate that although power plant 100 includes six combustor cans 104 and six sensors 106, embodiments of the present disclosure are not limited to configurations with six combustor cans 104 and six sensors 106. Rather, power plant 100 may include any number of combustor cans greater than two and any number of corresponding sensors. In one embodiment, power plant 100 is a 7FA gas turbine engine, commercially available from General Electric Company, Greenville, S.C., which has 14 combustor cans.

Sensors 106 are configured to monitor conditions, such as pressure, for corresponding combustor cans 104. In one embodiment, sensors 106 are dynamic pressure sensors configured to measure acoustic vibrations from corresponding combustor cans 104 and transmit signals indicative of combustion dynamics amplitude data and frequency data to a computing device 102.

In one embodiment, computer device 102 includes a display 108, at least one processor 110, and a memory area 112. Display 108 may be, for example, a capacitive touch screen display that is integrated into computing device 102 or external to computing device 102. User input functionality is provided in display 108 which acts as a user input selection device. Display 108 is configured to be responsive to a user pressing contact on display 108 to selectively perform functionality. Thus, a user can input, for example, a running state percentage threshold by contacting a surface of display 108 as well as other functions provided herein.

Memory area 112 stores, for example, combustor can history data, user defined thresholds, and acoustic vibration data corresponding to each of combustor cans 104. While combustor can history data, user defined thresholds, and acoustic vibration data are described as being stored in memory area 112, combustor can history data, user defined thresholds, and acoustic vibration data may be stored and accessed from a memory area remote from computing device 102. For example, combustor can history data, user defined thresholds, and acoustic vibration data may be stored in a cloud service, a database, or other memory area accessible by computing device 102. Such embodiments reduce the computational and storage burden on computing device 102.

In one embodiment, once one of combustor cans 104 is identified as having hardware damage, an alarm 114 may be initiated and/or an appropriate warning displayed to a user on, for example, display 108. Alarm 114 can be any type of signaling device, and, in some configurations, comprises one or more audible annunciators and/or warning lights, such as flashing strobe lights.

In one embodiment, processor 110 is transformed into a special purpose microprocessor by executing computer-executable instructions or by otherwise being programmed with instructions for monitoring gas turbine combustor hardware. For example, processor 110 is programmed with instructions such as illustrated below with reference to FIG. 2.

Figure 2:
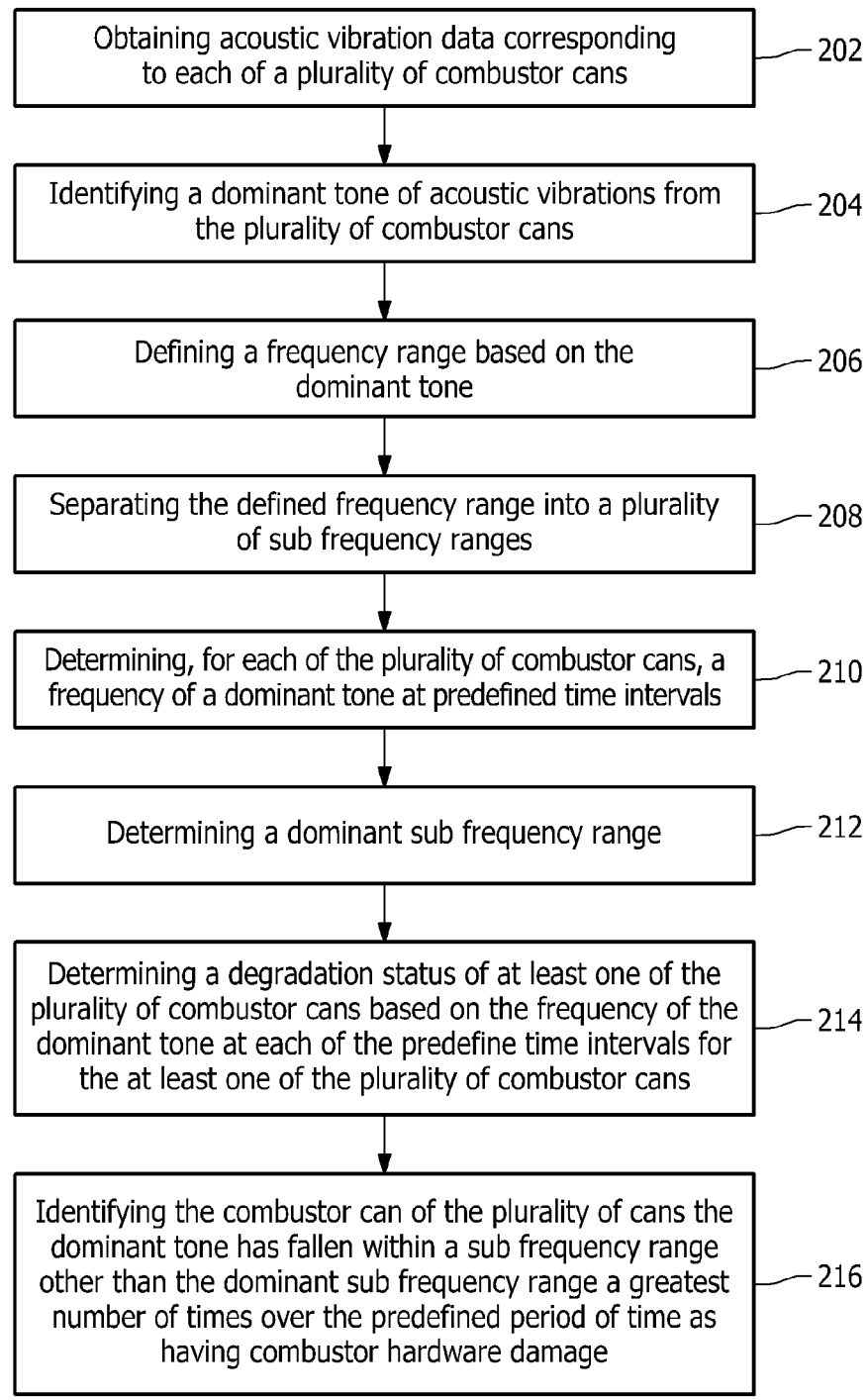
FIG. 2 is a process flow diagram for monitoring a degradation of gas turbine combustor hardware.

Referring now to FIG. 2, an exemplary flow chart illustrates a process for monitoring a degradation of combustor cans 104. As mentioned above, by monitoring changes in a dominant tone of acoustic vibrations from combustor cans 104, a degradation status of each combustor can may be determined based on a change in a frequency of the dominant tone over a period of time. Thus, at 202, acoustic vibration data (e.g., combustion dynamics amplitude data) corresponding to each combustor can 104 is obtained from, for example, sensors 106. In one embodiment, prior to analyzing acoustic vibration data, a determination is made as to whether power plant 100 is running at a steady state, that is, not in a transient state. Verifying that power plant 100 is running at a steady state is one way to ensure that measured acoustic vibration data from the measured acoustic vibrations of combustor cans 104 is accurate. In one embodiment, power plant 100 is running at a steady state if it is determined that power plant 100 is running at or above a defined running stage percentage threshold, for example, at or above 95%. However, one of ordinary skill in the art guided by the teachings herein will appreciate that a running state of any device or system may be specific to that device or system, and thus, different percentages may apply from device to device and from system to system.

At 204, a dominant tone (e.g., a frequency where a highest amount of energy lies) of the measured acoustic vibrations from combustor cans 104 is identified. In one embodiment, a frequency analysis using fast Fourier transform operation is used on a signal indicative of combustion dynamics amplitude data obtained from each sensor 106 to determine an energy level of each signal. At 206, a frequency range respective to the dominant tone is defined based on the dominant tone. In one embodiment, the defined frequency range is 120 Hz to 180 Hz. At 208, the defined frequency range is separated into a plurality of sub frequency ranges of, for example, 8 Hz. One of ordinary skill in the art guided by the teachings herein will appreciate that the sub frequency range of 8 Hz is merely exemplary as a range of 8 Hz is based on electronic board processing capability during system development. As such, sub frequency ranges other than 8 Hz may also be used. By defining a frequency range and separating the defined frequency range into sub frequency ranges enables data to be focused in specific areas of interest. For example, changes in the frequency of the dominant tone between the defined frequency range is determined to be more applicable than changes in the frequency of the dominant tone outside of the defined frequency range. To enable an identification of an onset of susceptible hardware degradation, a frequency of the dominant tone may be sampled at predefined time intervals in order to identify fluctuations in the frequency of the dominant tone in a particular combustor can 104. While a fluctuation in a frequency of the dominant tone occurring globally (e.g., across all combustor cans 104) is expected due to density changes, the methodology described herein adapts to non global behavior, for example, when one or more combustor cans 104 indicate a fluctuation in a frequency of the dominant tone while other combustor cans 104 do not. This local fluctuation may be indicative of combustor hardware damage in that particular combustor can 104, and thus, further action (e.g., an inspection of that particular combustor can 104) may be recommended.

As mentioned above, a fluctuation in a frequency of a dominant tone may be used as an indication of combustor hardware damage. In one embodiment, to determine a fluctuation of the dominant tone in each combustor can 104, acoustic vibrations are sampled at predefined time intervals to identify a frequency of the dominant tone with respect to each combustor can 104 at a particular period of time. As such, a number of times the dominant tone falls within a particular frequency range over a period of time can be identified. At 210, a frequency of the dominant tone is determined at predefined time intervals for each combustor can 104. At 212, a dominant sub frequency range is determined. In one embodiment, the dominant sub frequency range is determined by first determining, at each of the predefined time intervals, which of the plurality of sub frequency ranges the dominant tone falls within for each combustor can 104. A number of times the dominant tone has fallen within each of the plurality of sub frequency ranges is calculated over a predefined period of time (e.g., a day, a week, or even months) for each combustor can 104. For each combustor can 104, a sub frequency range of the plurality of sub frequency ranges the dominant tone has fallen within the greatest number of times over the predefined period of time is calculated, with the dominant sub frequency range being the frequency range the dominant tone fell within a greatest number of times over all combustor cans 104 during the predefined period of time.

At 214, a degradation status of at least one of combustor cans 104 is determined based on the frequency of the dominant tone at each of the predefine time intervals for the at least one of combustor cans 104. For example, at least one of combustor cans 104 is determined to have the dominant tone within a sub frequency range other than the dominant sub frequency range a greatest number of times over the predefined period of time, and is thus identified as having possible combustor hardware damage (see, for example, combustor can 3 in FIG. 4). Thereafter, a signal indicative of combustor hardware damage for the identified combustor can may be sent to a user. Thus, at 216, a combustor can the dominant tone has fallen within a sub frequency range other than the dominant sub frequency range a greatest number of times over the predefined period of time is identified as having combustor hardware damage. In one embodiment, once a combustor can is identified as having hardware damage, an alarm 114 may be initiated and/or an appropriate warning displayed to a user, on for example, display 108. Alarm 114 can be any type of signaling device, and, in some configurations, comprises one or more audible annunciators and/or warning lights, such as flashing strobe lights.

Figure 3:
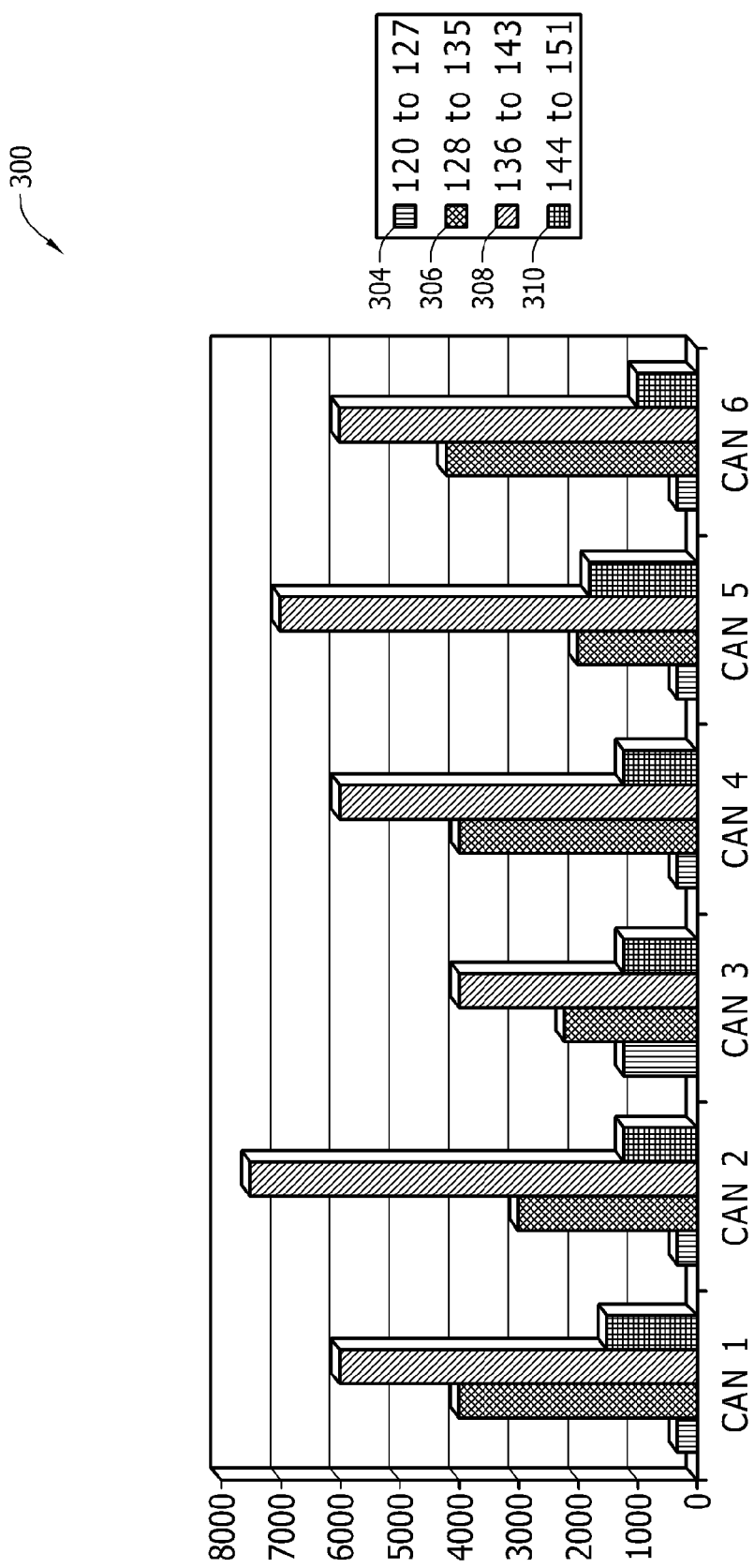
FIGS. 3 and 4 are graphs illustrating a frequency of a dominant tone over time.

With reference now to FIG. 3, a graph 300 illustrating a value of a dominant tone in a plurality of combustor cans over a period of time is provided. Graph 300 defines a frequency range respective to the dominant tone (e.g., 120 Hz to 151 Hz). The defined frequency range in graph 300 is separated into a plurality of sub frequency ranges of 8 Hz. For example, sub frequency range 304 is between 120 Hz to 127 Hz, sub frequency range 306 is between 128 Hz to 135 Hz, sub frequency range 308 is between 136 Hz to 143 Hz, sub frequency range 310 is between 144 Hz to 151 Hz. Data shown in graph 300 is representative of acoustic vibrations being sampled at predefined time intervals over a period of time. Each sampling identifies a frequency of the dominant tone with respect to each combustor can at a particular period of time, and a number of times the dominant tone falls within each of the sub frequency ranges over the period of time enables an identification of an onset of susceptible hardware degradation. For example, the sub frequency range the dominant tone falls within the greatest number of times for each combustor can is considered the dominant sub frequency range. As shown in FIG. 3, sub frequency range 308 is the dominant sub frequency range. That is, the frequency of the dominant tone fell within the sub frequency range of 136 Hz to 143 Hz the greatest number of times for each combustor can. In this example, each combustor can identifying sub frequency range 308 as the dominant sub frequency range is indicative of little or no damage to a respective combustor can. However, as illustrated below with reference to FIG. 4, as additional samplings of the acoustic vibrations are taken over time, combustor hardware damage may be present if another sub frequency range replaces sub frequency range 308 as the dominant sub frequency range in one or more combustor cans.

Figure 4:
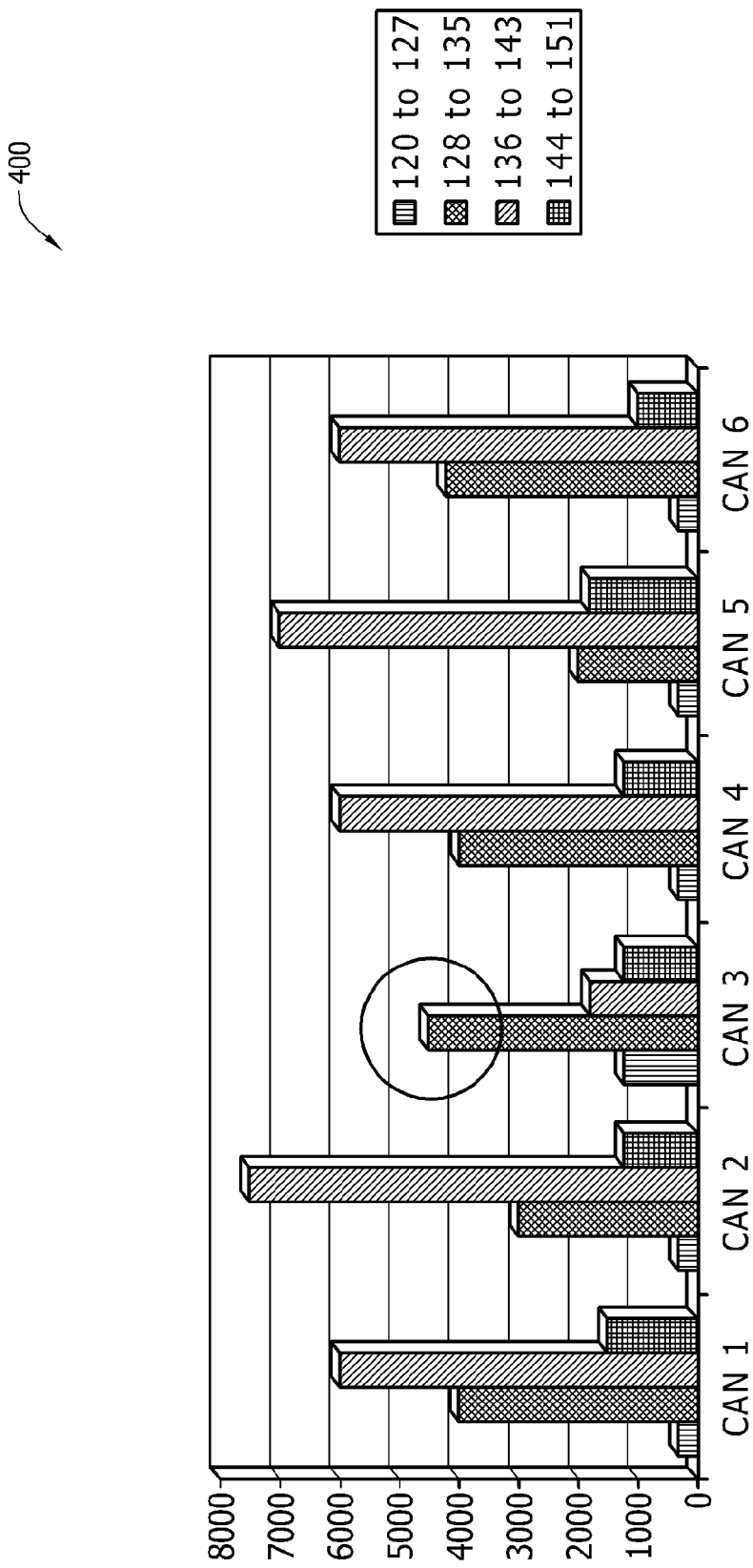

With reference now to FIG. 4, dominant sub frequency range 308 has been overcome by sub frequency range 306 in combustor can 3. That is, the number of times the frequency of the dominant tone fell within sub frequency range 308 decreased over time. This shift is indicative of possible combustor hardware damage, and more specifically, an increase in airflow caused by a crack in combustor can 3. For example, an increase in air flow caused by a crack may have increased airflow and caused a colder tone to appear. As such, identifying the shift of the dominating sub frequency ranges provides a proactive indication of initiation of hardware damage or propagation of existing damage.

Exemplary Operating Environment

A controller or computing device such as is described herein has one or more processors or processing units, system memory, and some form of computer readable media. By way of example and not limitation, computer readable media include computer storage media and communication media. Computer storage media include volatile and nonvolatile, removable and non-removable media implemented in any method or technology for storage of information such as computer readable instructions, data structures, program modules or other data. Communication media typically embody computer readable instructions, data structures, program modules, or other data in a modulated data signal, such as a carrier wave or other transport mechanism, and include any information delivery media. Combinations of any of the above are also included within the scope of computer readable media.

The controller/computer may operate in a networked environment using logical connections to one or more remote computers, such as a remote computer. Although described in connection with an exemplary computing system environment, embodiments of the present disclosure are operational with numerous other general purpose or special purpose computing system environments or configurations. The computing system environment is not intended to suggest any limitation as to the scope of use or functionality of any aspect of the present disclosure. Moreover, the computing system environment should not be interpreted as having any dependency or requirement relating to any one or combination of components illustrated in the exemplary operating environment. Examples of well known computing systems, environments, and/or configurations that may be suitable for use with aspects of the present disclosure include, but are not limited to, personal computers, server computers, hand-held or laptop devices, multiprocessor systems, microprocessor-based systems, set top boxes, programmable consumer electronics, mobile telephones, network PCs, minicomputers, mainframe computers, distributed computing environments that include any of the above systems or devices, and the like.

Embodiments of the present disclosure may be described in the general context of computer-executable instructions, such as program modules, executed by one or more computers or other devices. The computer-executable instructions may be organized into one or more computer-executable components or modules. Generally, program modules include, but are not limited to, routines, programs, objects, components, and data structures that perform particular tasks or implement particular abstract data types. Aspects of the present disclosure may be implemented with any number and organization of such components or modules. For example, aspects of the present disclosure are not limited to the specific computer-executable instructions or the specific components or modules illustrated in the figures and described herein. Other embodiments of the present disclosure may include different computer-executable instructions or components having more or less functionality than illustrated and described herein. Aspects of the present disclosure may also be practiced in distributed computing environments where tasks are performed by remote processing devices that are linked through a communications network. In a distributed computing environment, program modules may be located in both local and remote computer storage media including memory storage devices.

Aspects of the present disclosure transform a general-purpose computer into a special-purpose computing device when configured to execute the instructions described herein.

The order of execution or performance of the operations in embodiments of the present disclosure illustrated and described herein is not essential, unless otherwise specified. That is, the operations may be performed in any order, unless otherwise specified, and embodiments of the present disclosure may include additional or fewer operations than those disclosed herein. For example, it is contemplated that executing or performing a particular operation before, contemporaneously with, or after another operation is within the scope of aspects of the present disclosure.

When introducing elements of aspects of the present disclosure or the embodiments thereof, the articles "a," "an," "the," and "said" are intended to mean that there are one or more of the elements. The terms "comprising," "including," and "having" are intended to be inclusive and mean that there may be additional elements other than the listed elements.

Having described aspects of the present disclosure in detail, it will be apparent that modifications and variations are possible without departing from the scope of aspects of the present disclosure as defined in the appended claims. As various changes could be made in the above constructions, products, and methods without departing from the scope of aspects of the present disclosure, it is intended that all matter contained in the above description and shown in the accompanying drawings shall be interpreted as illustrative and not in a limiting sense.

This written description uses examples to disclose the claimed subject matter, including the best mode, and also to enable any person skilled in the art to practice the claimed subject matter, including making and using any devices or systems and performing any incorporated methods. The patentable scope of the present disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A power generation plant comprising:
    a plurality of combustor cans;
    one or more sensors configured to measure acoustic vibration data from the plurality of combustor cans; and
    a controller comprising a processor, the processor programmed to:
        determine, for each of the plurality of combustor cans based on the acoustic vibration data, a frequency of a dominant tone at a plurality of predefined time intervals, the dominant tone being a frequency where a highest amount of energy lies;
        identify, for each combustor can at each of the predefined time intervals, which of a plurality of sub frequency ranges the dominant tone falls within;
        identify a dominant sub frequency range as one of the plurality of sub frequency ranges into which the greatest number of dominant tones falls for all combustor cans throughout the plurality of predefined time intervals; and
        determine a degradation status of at least one of the plurality of combustor cans based on a number of the predefined time intervals for which the dominant tone of the at least one combustor can is not within the dominant sub frequency range.

2. A power generation plant in accordance with claim 1, wherein acoustic vibration data comprises combustion dynamics amplitude data.

3. A power generation plant in accordance with claim 2, wherein the processor is further programmed to perform a fast Fourier transform on the combustion dynamics amplitude data associated with each of the plurality of combustor cans to determine frequency data for each of the plurality of combustor cans.

4. A power generation plant in accordance with claim 1, wherein determining a degradation status of at least one of the plurality of combustor cans further comprises:
    defining a frequency range based on the dominant tone; and
    separating the defined frequency range into the plurality of sub frequency ranges.

5. A power generation plant in accordance with claim 1, wherein determining a degradation status of at least one of the plurality of combustor cans comprises:
    identifying, as having combustor hardware damage, a combustor can of the plurality of combustor cans that has a greatest number of the predefined time intervals in which the dominant tone of the combustor can is not within the dominant sub frequency range.

6. A power generation plant in accordance with claim 5, wherein determining a degradation status of at least one of the plurality of combustor cans further comprises sending a signal indicative of combustor hardware damage for the identified combustor can.

7. A power generation plant in accordance with claim 5, wherein the combustor hardware damage is a crack enabling an increase in air flow leaning out a fuel to air ratio.

8. A power generation plant in accordance with claim 1, wherein the processor is further programmed to determine whether the gas turbine is running at a steady state; and
    if the gas turbine is running at a steady state, the processor is configured to receive the measured acoustic vibration data corresponding to each of the plurality of combustor cans.

9. A method for monitoring gas turbine combustor hardware, the method comprising:
    obtaining, by a controller from sensors coupled to the gas turbine combustor hardware, acoustic vibration data corresponding to each of a plurality of combustor cans;
    determining, by the controller for each of the plurality of combustor cans based on the acoustic vibration data, a frequency of a dominant tone at a plurality of predefined time intervals, the dominant tone being a frequency where a highest amount of energy lies;
    identifying, by the controller for each combustor can at each of the predefined time intervals, which of a plurality of sub frequency ranges the dominant tone falls within;
    identifying, by the controller, a dominant sub frequency range as one of the plurality of sub frequency ranges into which the greatest number of dominant tones falls for all combustor cans throughout the plurality of predefined time intervals; and
    determining, by the controller, a degradation status of at least one of the plurality of combustor cans based on a number of the predefined time intervals for which the dominant tone of the at least one combustor can is not within the dominant sub frequency range.

10. A method in accordance with claim 9, wherein acoustic vibration data comprises combustion dynamics amplitude data.

11. A method in accordance with claim 10, further comprising performing, by the controller, a fast Fourier transform on the combustion dynamics amplitude data associated with each of the plurality of combustor cans to determine frequency data for each of the plurality of combustor cans.

12. A method in accordance with claim 9, wherein determining a degradation status of at least one of the plurality of combustor cans further comprises:
    defining a frequency range based on the dominant tone; and
    separating the defined frequency range into the plurality of sub frequency ranges.

13. A method in accordance with claim 9, wherein determining a dominant sub frequency range determining a degradation status of at least one of the plurality of combustor cans comprises:

identifying by the controller, as having combustor hardware damage, a combustor can of the plurality of combustor cans that has a greatest number of the predefined time intervals in which the dominant tone of the combustor can is not within the dominant sub frequency range.

14. A method in accordance with claim 13, wherein determining a degradation status of at least one of the plurality of combustor cans further comprises sending a signal indicative of combustor hardware damage for the identified combustor can.

15. A method in accordance with claim 13, wherein the combustor hardware damage is a crack enabling an increase in air flow leaning out a fuel to air ratio.

16. A method in accordance with claim 9, further comprising determining, by the controller, whether the gas turbine is running at a steady state; and
if the gas turbine is running at a steady state, accessing, by the controller, the acoustic vibration data corresponding to each of the plurality of combustor cans.

17. A system for monitoring gas turbine combustor hardware, the system comprising:
a combustor comprising a plurality of combustor cans;
one or more sensors configured to measure combustion dynamics amplitude data from acoustic vibrations corresponding to each of the plurality of combustor cans; and
a controller comprising a processor, the processor programmed to:
determine frequency data from the measured combustion dynamics amplitude data;
determine, for each of the plurality of combustor cans based on the frequency data, a frequency of a dominant tone at a plurality of predefined time intervals, the dominant tone being a frequency where a highest amount of energy lies;
identify, for each combustor can at each of the predefined time intervals, which of a plurality of sub frequency ranges the dominant tone falls within;
identify a dominant sub frequency range as one of the plurality of sub frequency ranges into which the greatest number of dominant tones falls for all combustor cans throughout the plurality of predefined time intervals; and
determine a degradation status of at least one of the plurality of combustor cans based on a number of predefined time intervals for which the dominant tone of the at least one combustor can is not within the dominant sub frequency range.

18. A system in accordance with claim 17, wherein determining a degradation status of at least one of the plurality of combustor cans comprises;
defining a frequency range based on the dominant tone; and
separating the defined frequency range into the plurality of sub frequency ranges.

19. A system in accordance with claim 17, wherein determining a degradation status of at least one of the plurality of combustor cans comprises:
identifying, as having combustor hardware damage, a combustor can of the plurality of combustor cans that has a greatest number of predefined time intervals for which the dominant tone of the combustor can is not within the dominant sub frequency range.

20. A system in accordance with claim 19, further comprising an alarm configured to activate in response to a signal received from the processor, the signal indicative of combustor hardware damage for the identified combustor can.

* * * * *